US009228166B2

(12) United States Patent
Barrett et al.

(10) Patent No.: US 9,228,166 B2
(45) Date of Patent: Jan. 5, 2016

(54) ROCKABLE BIOCONTAINER

(75) Inventors: Timothy Alan Barrett, Southsea (GB);
Alison Jane West, Hampshire (GB);
Kenneth Roy Weight, Hampshire (GB);
Adam Peter Westwood, Hampshire
(GB); Daniel James Kesselaar, London
(GB)

(73) Assignee: Pall Corporation, Port Washington, NY (US)

( * ) Notice: Subject to any disclaimer, the term of this patent is extended or adjusted under 35 U.S.C. 154(b) by 0 days.

(21) Appl. No.: 13/331,212

(22) Filed: Dec. 20, 2011

(65) Prior Publication Data

US 2013/0157355 A1    Jun. 20, 2013

(51) Int. Cl.
*C12M 3/00* (2006.01)
*C12M 1/00* (2006.01)
*C12M 3/06* (2006.01)

(52) U.S. Cl.
CPC ............. *C12M 23/46* (2013.01); *C12M 23/14* (2013.01); *C12M 23/48* (2013.01); *C12M 27/16* (2013.01)

(58) Field of Classification Search
CPC ............... B65D 2590/046; B67D 2001/0827;
C12M 23/14; C12M 23/46; C12M 23/48;
C12M 27/16
USPC ............... 435/289.1; 366/208–209, 144, 212
See application file for complete search history.

(56) References Cited

U.S. PATENT DOCUMENTS

| 1,772,073 | A | * | 8/1930 | Drucker ..................... 366/231 |
| 2,610,041 | A | * | 9/1952 | Stahl ........................... 366/215 |
| 6,190,913 | B1 | | 2/2001 | Singh |
| 6,338,569 | B1 | * | 1/2002 | McGill ....................... 366/144 |
| 2003/0036192 | A1 | | 2/2003 | Singh |
| 2007/0185472 | A1 | | 8/2007 | Baumfalk et al. |
| 2008/0118974 | A1 | | 5/2008 | Martin et al. |
| 2009/0236338 | A1 | * | 9/2009 | Elton et al. ............... 220/23.83 |
| 2009/0236344 | A1 | | 9/2009 | McRobbie et al. |
| 2010/0129899 | A1 | * | 5/2010 | Oosterhuis et al. ........ 435/288.7 |
| 2011/0014689 | A1 | | 1/2011 | Gandlur |
| 2011/0151551 | A1 | | 6/2011 | Yi et al. |
| 2011/0151552 | A1 | | 6/2011 | Jiang et al. |

FOREIGN PATENT DOCUMENTS

| GB | 2 411 178 A | 8/2005 |
| JP | 2008-513034 A | 5/2008 |
| JP | 2010-539936 A | 4/2009 |
| JP | 2010-529854 A | 9/2010 |
| WO | WO 2005/111192 A1 | 11/2005 |
| WO | WO 2007/001173 A2 | 1/2007 |

(Continued)

OTHER PUBLICATIONS

Australian Patent Examination Report, Application No. 2012268920, dated Jul. 31, 2013.

(Continued)

*Primary Examiner* — Michael Hobbs
*Assistant Examiner* — Liban Hassan
(74) *Attorney, Agent, or Firm* — Leydig, Voit & Mayer

(57) ABSTRACT

Biocontainers, as well as methods and platforms for rocking the biocontainers, are disclosed.

14 Claims, 9 Drawing Sheets

(56) References Cited

FOREIGN PATENT DOCUMENTS

| | | | |
|---|---|---|---|
| WO | WO 2008/153401 A1 | | 12/2008 |
| WO | WO 2009/042432 A1 | | 4/2009 |
| WO | WO 2009042432 A1 | * | 4/2009 |
| WO | WO 2010/056555 A1 | | 5/2010 |
| WO | WO 2011/005773 A2 | | 1/2011 |

OTHER PUBLICATIONS

European Search Report, Application No. 12 19 6956.2-1501, dated May 5, 2013.
Notice of Reasons for Rejection, JP Application No. P2012-271521, dated Jan. 28, 2014.

* cited by examiner

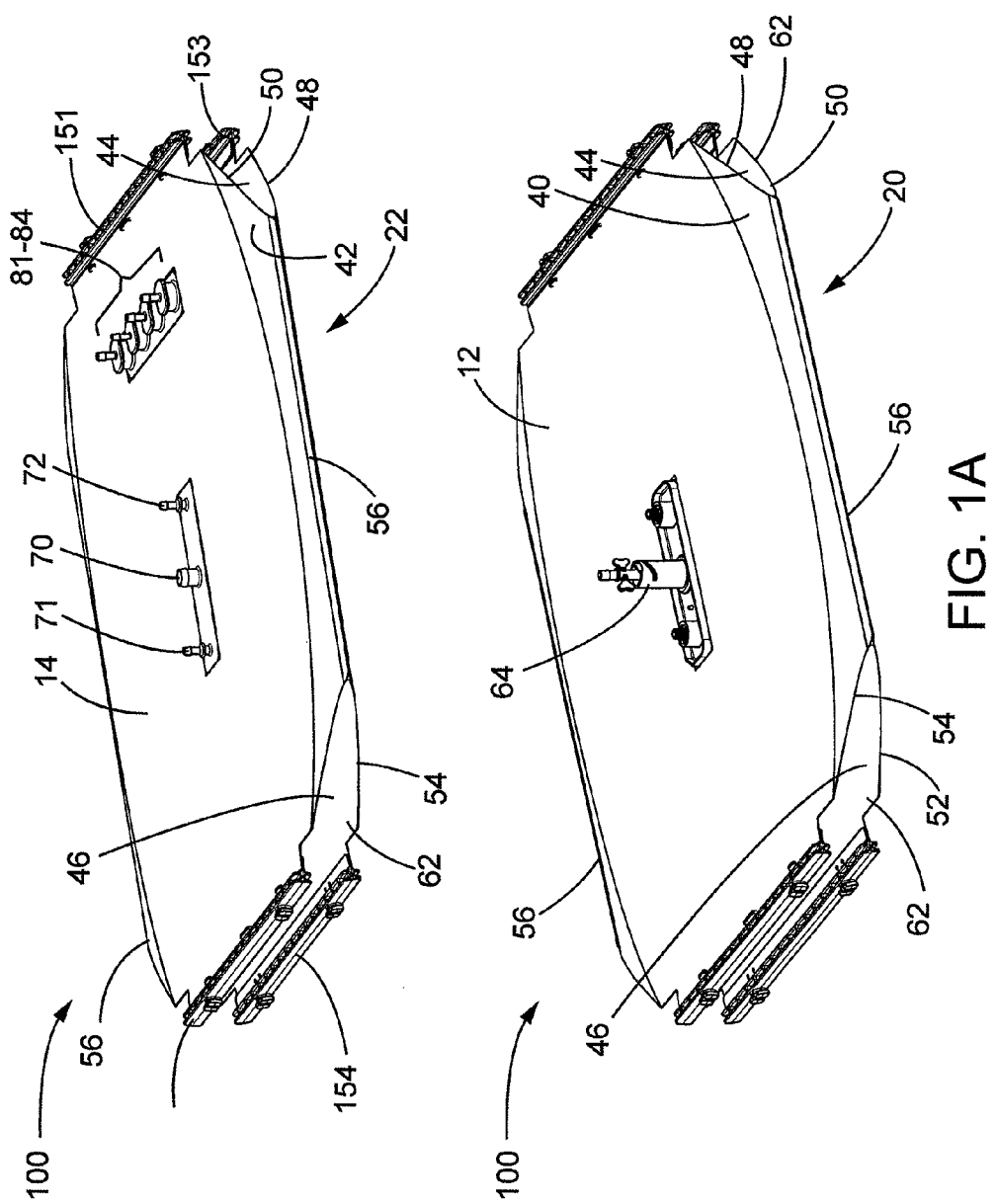

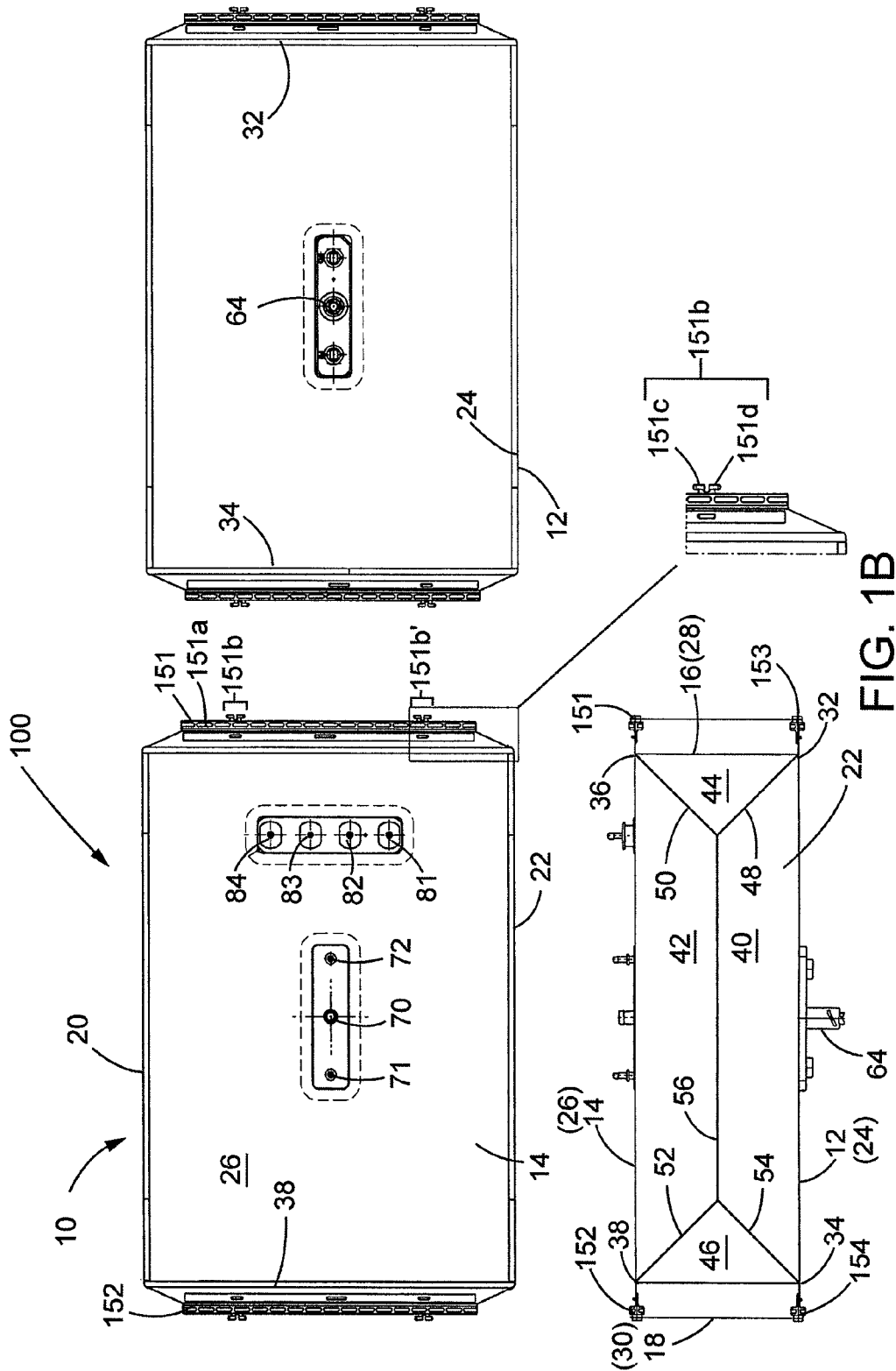

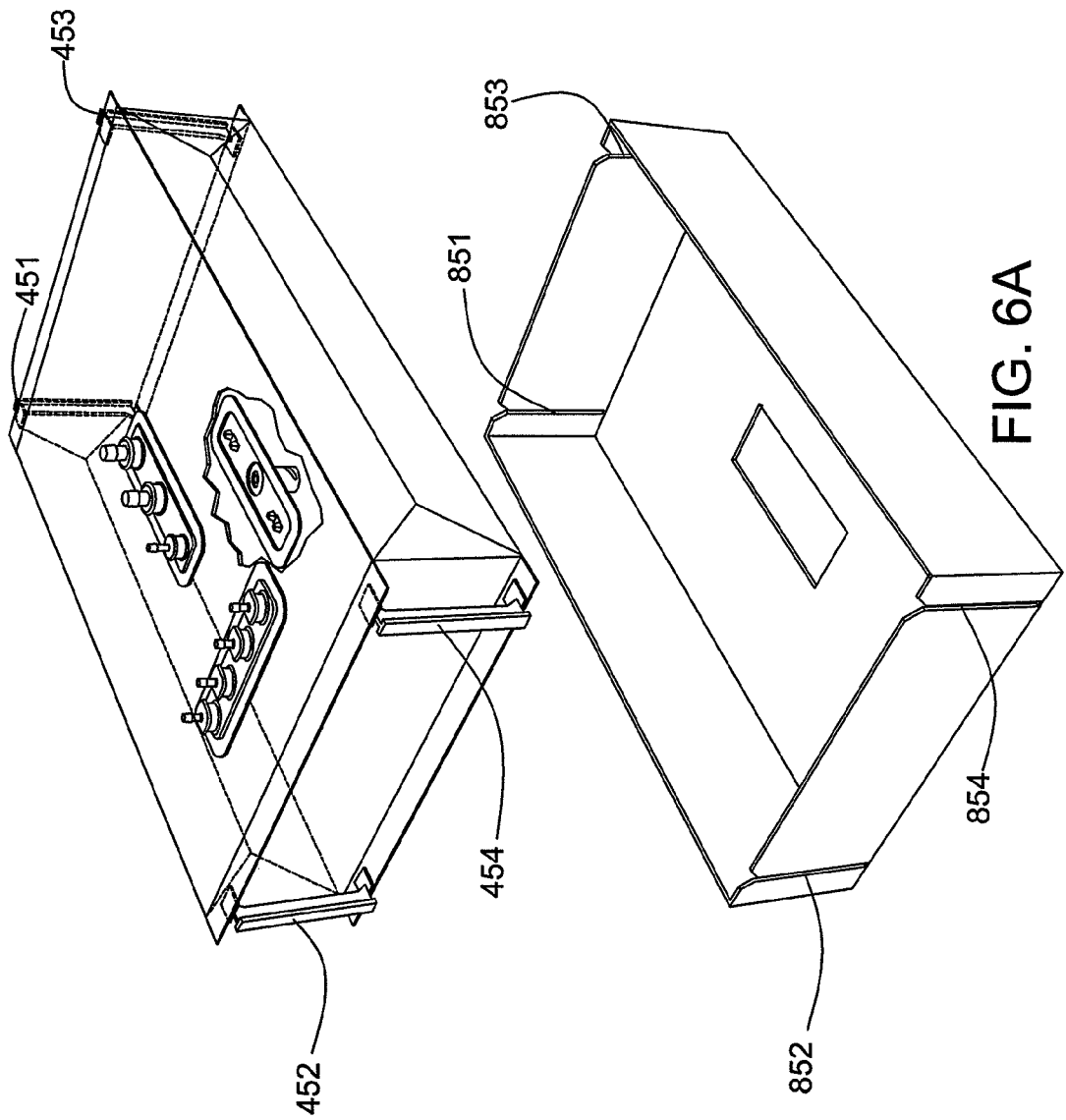

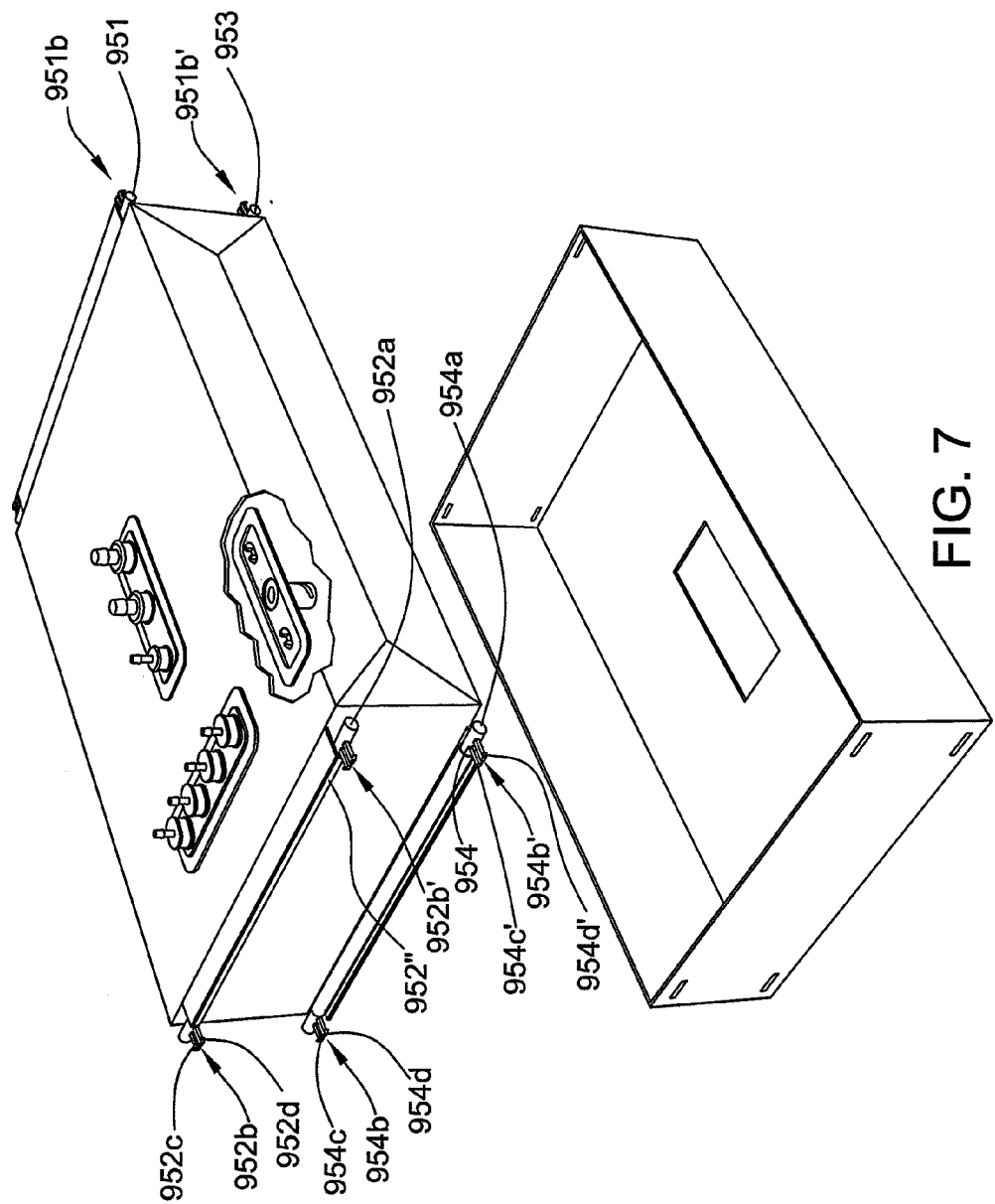

US 9,228,166 B2

ROCKABLE BIOCONTAINER

BACKGROUND OF THE INVENTION

Cell culturing is used for a variety of applications, e.g., in the biotechnology and pharmaceutical industry to produce, for example, antibodies, proteins, vaccines, and gene therapy products. Typically, for processing fluids with volumes of more than 1 or 2 liters, e.g., for processing fluids with volumes of about 10 liters or more, for example, about 20 to about 500 liters, or more, bioreactors are used.

However, there is a need in the art for bioreactors and systems that provide improved mixing (e.g., of oxygen, pH, and/or the substrate) while minimizing damage to the cells. These and other advantages of the present invention will be apparent from the description as set forth below.

BRIEF SUMMARY OF THE INVENTION

An embodiment of the invention provides a biocontainer, comprising a closed container comprising a bottom wall, a top wall, first and second opposing side walls, and third and fourth opposing side walls, the side walls being joined to the top wall and the bottom wall; and at least two ports, wherein the biocontainer has a substantially rectangular cuboid form, and the biocontainer further comprises at least first and second brackets secured to the container, wherein the first and second brackets are releasably engageable with a platform suitable for supporting the biocontainer. Preferably, the biocontainer further comprises at least third and fourth brackets secured to the container, wherein the third and fourth brackets are releasably engageable with a platform suitable for supporting the biocontainer.

In an embodiment, the first bracket is secured to the container near a joint between the top wall and the first side wall, and the second bracket is secured to the container near a joint between the top wall and the second opposing side wall. The embodiment can further comprise brackets secured to the bottom wall of the container and/or secured to opposing side walls of the container. For example, an embodiment of the biocontainer further comprises a third bracket secured to the container near a joint between the bottom wall and the first side wall, and a fourth bracket secured to the container near a joint between the bottom wall and the second opposing side wall.

In yet another embodiment comprising at least four brackets, the first and third brackets are each secured to the container near a joint between the top wall and the first side wall, and near a joint between the bottom wall and the first side wall, and the second and fourth brackets are each secured to the container near a joint between the top wall and the second opposing side wall, and near a joint between the bottom wall and the second opposing side wall.

In an embodiment, a method of processing a cell culture-containing fluid comprises rocking a biocontainer comprising a substantially cuboid-shaped closed container on a platform along one or more degrees of freedom, wherein the container contains at least a liquid culture medium and cells, and wherein biocontainer further comprises at least first and second brackets engaged with the platform. A preferred embodiment of the method comprises rocking the biocontainer a platform along at least first and second substantially horizontal pivot axes that are perpendicular to one another, wherein the biocontainer further comprises at least first and second brackets engaged with the platform. In a more preferred embodiment of the method, the biocontainer further comprises at least third and fourth brackets engaged with the platform while the biocontainer is rocked. Embodiments of the method can further comprise draining at least some of the fluid from the container, releasing the engagement between the brackets and the platform, and removing the biocontainer from the platform.

In yet another embodiment, a rockable platform for rocking a substantially cuboid-shaped container is provided, wherein the rockable platform is suitable for use with a rocking apparatus, and the platform includes at least a first bracket engagement portion and a second bracket engagement portion. In a more preferred embodiment, the platform further comprises at least a third bracket engagement portion and a fourth bracket engagement portion. In some embodiments, the platform further comprises a heater for heating the container.

BRIEF DESCRIPTION OF THE SEVERAL VIEWS OF THE DRAWING(S)

FIG. 1 shows a bioreactor according to an embodiment of the present invention, further comprising first, second, third, and fourth brackets. FIG. 1A shows top and bottom views of the bioreactor in a partially folded or collapsed state, FIG. 1B shows top, bottom, and side views, with the side view showing the bioreactor in a filled or expanded state.

FIG. 2 also shows an illustrative apparatus comprising the rocking platform.

FIG. 6 shows additional embodiments of a bioreactor according to the invention, comprising at least four brackets, also showing a rocking platform for receiving the bioreactors, the platform further comprising bracket engagement portions, including "I-shaped" brackets engaging with a slot. FIG. 6A shows a platform including integral slots.

FIG. 7 shows yet another embodiment of a bioreactor according to the invention, comprising at least four brackets, wherein the brackets include sleeves comprising the bracket body therein, also showing a rocking platform.

DETAILED DESCRIPTION OF THE INVENTION

Figure 2:
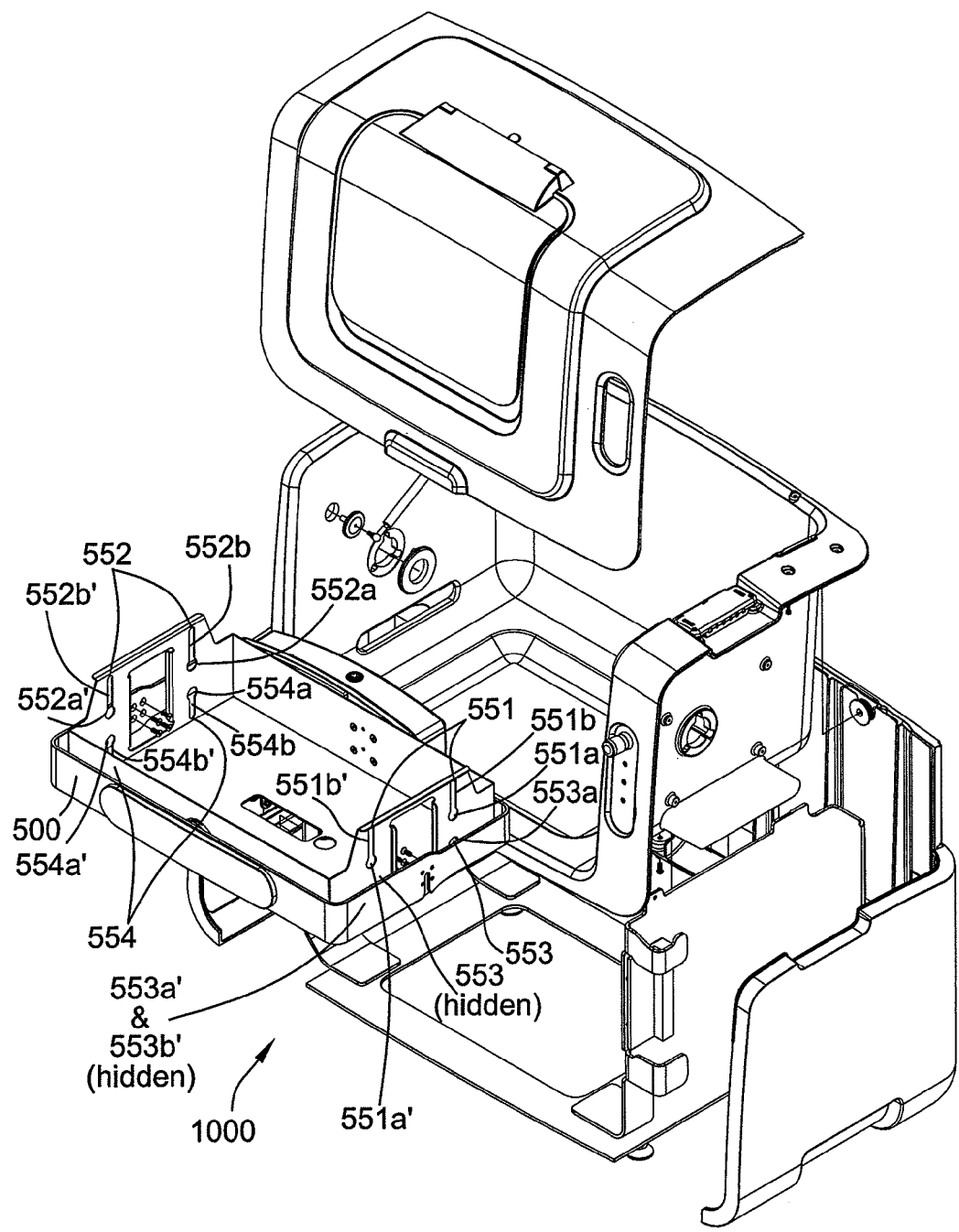
FIG. 2 shows an illustrative rocking platform, including bracket engagement portions.

Advantageously, a disposable biocontainer having a substantially rectangular cuboid form, and further comprising brackets secured to the container, wherein the brackets are releasably engageable with a platform suitable for supporting the biocontainer, provides efficient mixing of the contents of the biocontainer during rocking, while maintaining the substantially rectangular cuboid form. In addition to helping maintain the form and/or shape of the biocontainer, the use of a plurality of brackets minimizes movement of the biocontainer during rocking, thus minimizing stress, rubbing and/or abrasion to the biocontainer (e.g., stress, rubbing and/or abrasion with respect to the seals and/or the walls of the biocontainer).

Additionally, mixing can be quickly and efficiently achieved while minimizing damage to shear-sensitive cells, providing optimal cell growth and productivity.

In contrast with systems wherein a "pillow-shaped" container is rocked back and forth along one axis running along the center of the container, resulting in different rates in mixing from front to back in the container as compared to side to side, the use of presently described bioreactor rocked along two substantially horizontal pivot axes provides faster mixing throughout the contents of the biocontainer. Thus, pH control is improved, as added acid or base (to modulate the pH) is quickly dispersed throughout the biocontainer, added nutrients are quickly distributed more uniformly through the biocontainer, and oxygen (e.g., transferred from the head space) is efficiently distributed to the cells in the biocontainer.

Without being limited to any particular mechanism, it is believed that the improved mixing is a result of the combination of fluid flow along a longer path when rocked in one direction, and fluid flow along a shorter path when rocked in an approximate perpendicular direction, e.g., the fluid traveling along the longer path "folds into" the bulk fluid flows throughout the depth of the biocontainer when the fluid contacts the short-side face of the biocontainer.

In another advantage, a smaller footprint biocontainer can be used when compared to conventional pillow-shaped containers when culturing equivalent volumes.

An embodiment of the invention provides a biocontainer, comprising a closed container comprising a bottom wall, a top wall, first and second opposing side walls, and third and fourth opposing side walls, the side walls being joined to the top wall and the bottom wall; and at least two ports, wherein the biocontainer has a substantially rectangular cuboid form, and the biocontainer further comprises at least first and second brackets secured to the container, wherein the first and second brackets are releasably engageable with a platform suitable for supporting the biocontainer. Preferably, the biocontainer further comprises at least third and fourth brackets secured to the container, wherein the third and fourth brackets are releasably engageable with a platform suitable for supporting the biocontainer. Typically, in those embodiments including at least four brackets, at least two brackets are associated with a lower portion of the biocontainer, and at least two brackets are associated with an upper portion of the biocontainer.

In an embodiment, the first bracket is secured to the container near a joint between the top wall and the first side wall, and the second bracket is secured to the container near a joint between the top wall and the second opposing side wall. The embodiment can further comprise brackets secured to the bottom wall of the container and/or secured to opposing side walls of the container. For example, an embodiment of the biocontainer further comprises a third bracket secured to the container near a joint between the bottom wall and the first side wall, and a fourth bracket secured to the container near a joint between the bottom wall and the second opposing side wall. In other illustrative embodiments, the biocontainer further comprises a third bracket secured to the first side wall and a fourth bracket secured to the second opposing side wall; or at least a pair of third brackets secured to the first side wall and at least a pair of fourth brackets secured to the second opposing side wall; or the biocontainer further comprises at least a third bracket secured to the bottom wall; or the biocontainer further comprises a third bracket secured to the bottom wall near the first side wall and a fourth bracket secured to the bottom wall near the second opposing side wall; or the biocontainer further comprises at least a pair of third brackets secured to the bottom wall near the first side wall and at least a pair of fourth brackets secured to the bottom wall near the second opposing side wall.

In yet another embodiment comprising at least four brackets, the first and third brackets are each secured to the container near a joint between the top wall and the first side wall, and near a joint between the bottom wall and the first side wall, and the second and fourth brackets are each secured to the container near a joint between the top wall and the second opposing side wall, and near a joint between the bottom wall and the second opposing side wall.

In accordance with embodiments of the invention, the biocontainer brackets are releasably engagable with bracket engaging portions on a rockable platform, and the biocontainer, containing a cell culture fluid (and preferably cells therein), can be rocked while the brackets are engaged with the bracket engaging portions.

A method of processing a cell culture-containing fluid provided by an embodiment of the invention comprises rocking a biocontainer comprising a substantially cuboid-shaped closed container, on a platform along at least one degree of freedom about a pivot point, preferably, rocking the biocontainer along at least first and second substantially horizontal pivot axes that are perpendicular to one another, wherein the container contains at least a liquid culture medium and cells, and wherein biocontainer further comprises at least first and second brackets engaged with the platform. In a more preferred embodiment of the method, the biocontainer further comprises at least third and fourth brackets engaged with the platform while the biocontainer is rocked. Embodiments of the method further comprise draining at least some of the fluid from the biocontainer, releasing the engagement between the brackets and the platform, and removing the biocontainer from the platform.

In yet another embodiment, a rockable platform for receiving and rocking a substantially cuboid-shaped container is provided, wherein the rockable platform is suitable for use with a rocking apparatus, and the platform includes at least a first bracket engagement portion and a second bracket engagement portion arranged to releasably engage the brackets secured to the biocontainer. In a more preferred embodiment of the platform, the platform further comprises at least a third bracket engagement portion and a fourth bracket engagement portion. Accordingly, the rectangular cuboid shape and/or form of the biocontainer is maintained while the biocontainer is rocked on the platform. In some embodiments, the platform further comprises a heater for heating the container.

A wide variety of cells can be cultured in accordance with embodiments of the invention, e.g., animal, plant, microbial and insect cells, in free suspension and/or in anchorage-dependent systems. Embodiments of the invention are also suitable for virus and pathogen cultivation.

The temperature of the cell culture fluid can be controlled, e.g., by placing the biocontainer and apparatus including a rocking platform inside a temperature controlled chamber, or by placing the biocontainer on the platform wherein the platform further comprises includes a heater or heating element.

Typically, the biocontainer comprises a closed container comprising a bottom wall, a top wall, and four side walls of a substantially rectangular configuration, made of a flexible sheet material, comprising a plurality of ports, the bottom, top, and side walls being provided by four separate sheets which are joined together at their edges, wherein a first sheet forms the bottom wall, a second sheet forms the top wall, and a third and fourth sheet form a first and a second side wall at two opposite sides of the container, the four sheets each further comprising, in addition to the portions forming the bottom, top and first and second sides, integrally formed triangular or trapezoid shaped wall portions at opposite ends thereof, the triangular or trapezoid shaped wall portions form, when joined together, a third and fourth side all, respectively.

As used herein, the term "closed container" or "closed biocontainer" means the container is sealed off against the environment and communication with the interior of the biocontainer is limited to the port or ports. Thus, fluid can be processed without the need to compromise the sterile integrity of the biocontainer, which is of particular importance where the biocontainer is to form part of a sterile system. A closed or sterile system can be as originally made, or result from the connection of system components using what are known as, for example, "sterile docking" devices.

The use of a disposable closed biocontainer wherein the inner layer is the only contact surface for the cells, provides excellent containment and eliminates labor intensive cleaning and sterilization.

Typically, the top wall of the biocontainer accommodates a plurality of ports, and the bottom wall accommodates at least one port. Preferably, the biocontainer includes one or more gas ports arranged at or near the center of the top wall, and/or one or more liquid ports arranged non-centrally in the top wall. Ports can be used to feed fluids separately into the container and/or to provide access for testing equipment and/or sampling. The use of centrally arranged gas ports can minimize or eliminate the chance that the port(s) will be blocked by liquid while the biocontainer is being rocked, and the use of non-central liquid ports can allow for more efficient mixing as the introduced liquid is placed in contact with the liquid moving in the rocked container. Alternatively, or additionally, the biocontainer has a drain port arranged at or near the center of the bottom wall, which can provide for more efficient drainage, particularly when the biocontainer forms a slightly domed shape when inflated.

Preferably, the biocontainer is delivered in a flat state to the market, the first and second side walls comprising fold lines at a position about half height thereof, the first and second side walls being folded inwards, and the third and fourth walls formed of the joined triangular or trapezoid shaped portions are folded outwards. If desired, the biocontainer can be sealed in another container, such as a package, for ease in sterilization and/or shipping.

The flat biocontainers can be easily set up in or on the rockable platform, e.g., wherein the outwardly folded third and fourth sidewalls are folded outwards.

Each of the components of the invention will now be described in more detail below, wherein like components have like reference numbers.

FIG. 1 shows an embodiment of a biocontainer 100 comprising a closed container 10 comprising a bottom wall 12, a top wall 14, a first side wall 16, a second side wall 18, a third side wall 20, a fourth side wall 22, a plurality of ports 70, 71, 72 (for convenience, ports 70-72 will be referred to as "gas ports"), 81, 82, 83, and 84 (for convenience, ports 81-84 will be referred to as "liquid ports"), accommodated by the first wall, a port 64 accommodated by the bottom wall, a first bracket 151, a second bracket 152, a third bracket 153, and a fourth bracket 154, wherein the brackets are secured to the container. FIG. 1A shows container 10 in a substantially folded not yet completely laid flat state, where the side walls 16 and 18 are folded in inwardly along fold lines 58 and 60, respectively. FIG. 1B shows, in a side view, the biocontainer 100 in an expanded state (liquid cell medium not shown).

The container 10 is generally made from four pieces of a flexible plastic sheet material, where a first sheet 24 provides for the bottom wall 12, a second sheet 26 provides for the top wall 14, a third sheet 28 provides for the first side wall 16 and a fourth sheet 30 provides for a second side wall 18, the first and second side walls 16, 18 being located on opposite side of the container 10. Each one of the first, second, third and fourth sheet materials 24, 26, 28 and 30 have a substantial rectangular shape. Opposite edges of the sheets 28 and 30 forming the opposing side walls are joined with edges of the bottom and top wall sheet materials 24, 26 by joints or seams 32, 34, 36 and 38 resulting in a sleeve-like structure.

Each one of the sheet materials comprise at opposite ends thereof triangular or trapezoid shaped wall portions 40, 42, 44 and 46. These wall portions 40, 42, 44, 46 are joined to one another to form the opposing third and fourth side walls 20, 22. The joined portions are represented as seams 48, 50, 52, 54, 56. The container is now in a closed state. The third and fourth side walls 20, 22 are folded outwardly from the body of container 10 and laid flat as substantially triangular or trapezoid shaped flaps 62.

In accordance with the embodiment illustrated in FIG. 1, the biocontainer further comprises a first bracket 151 secured to the container near (shown connected to) a joint or seam 36 between the top wall 14 and the first side wall 16, a second bracket 152 secured to the container near a joint or seam 38 between the top wall 14 and the second opposing side wall 18, a third bracket 153 secured to the container near a joint or seam 32 between the bottom wall 12 and the first side wall 16, and a fourth bracket 154 secured to the container near a joint or seam 34 between the bottom wall 12 and the second opposing side wall 18.

In the embodiment illustrated in FIG. 1, each bracket comprises a body and two projections, each projection comprising a pair of angled lugs facing in opposing directions. Thus, first bracket 151 comprises a body 151a, first projection 151b comprising first projection lugs 151c and 151d, wherein the lugs 151c and 151d face in opposing directions, and second projection 151b' comprising second projection lugs 151c' and 151d', wherein the lugs 151c' and 151d' face in opposing directions. The illustrated second, third, and fourth brackets are similar, e.g., second bracket 152 comprises a body 152a, first projection 152b comprising first projection lugs 152c and 152d, wherein the lugs 152c and 152d face in opposing directions, and second projection 152b' comprising second projection lugs 152c' and 152d', wherein the lugs 152c' and 152d' face in opposing directions.

Preferably, the brackets are permanently secured to the biocontainers, e.g., by an adhesive, a solvent, laser welding, radio frequency sealing, ultrasonic sealing and/or heat sealing, as is known in the art.

As will be explained in more detail below, the biocontainer brackets are releasably engaged with bracket engaging portions on a rockable platform, and the biocontainer, containing a cell culture fluid (liquid cell medium) and cells therein is rocked for a desired period.

For example, referring to FIG. 2, showing an illustrative apparatus 1000 comprising a rockable platform 500 including first bracket engagement portion 551 comprising enlarged opening 551a and slot 551b, and enlarged opening 551a' and slot 551b'; second bracket engagement portion 552 comprising enlarged opening 552a and slot 552b, and enlarged opening 552a' and slot 552b'; third bracket engagement portion 553 comprising enlarged opening 553a and slot 553b (hidden from view by platform 500), and enlarged opening 553a' and slot 553b'; and fourth bracket engagement portion 554 comprising enlarged opening 554a and slot 554b, and enlarged opening 554*a*' and slot 554*b*' (both hidden from view by platform 500); the first biocontainer bracket 151 (shown in FIG. 1B) is releasably engaged with the first bracket engagement portion, and the second, third, and fourth biocontainer brackets (brackets 152-154 shown in FIG. 1B) are releasably engaged with the respective second, third, and fourth bracket engagement portions.

Figure 3:
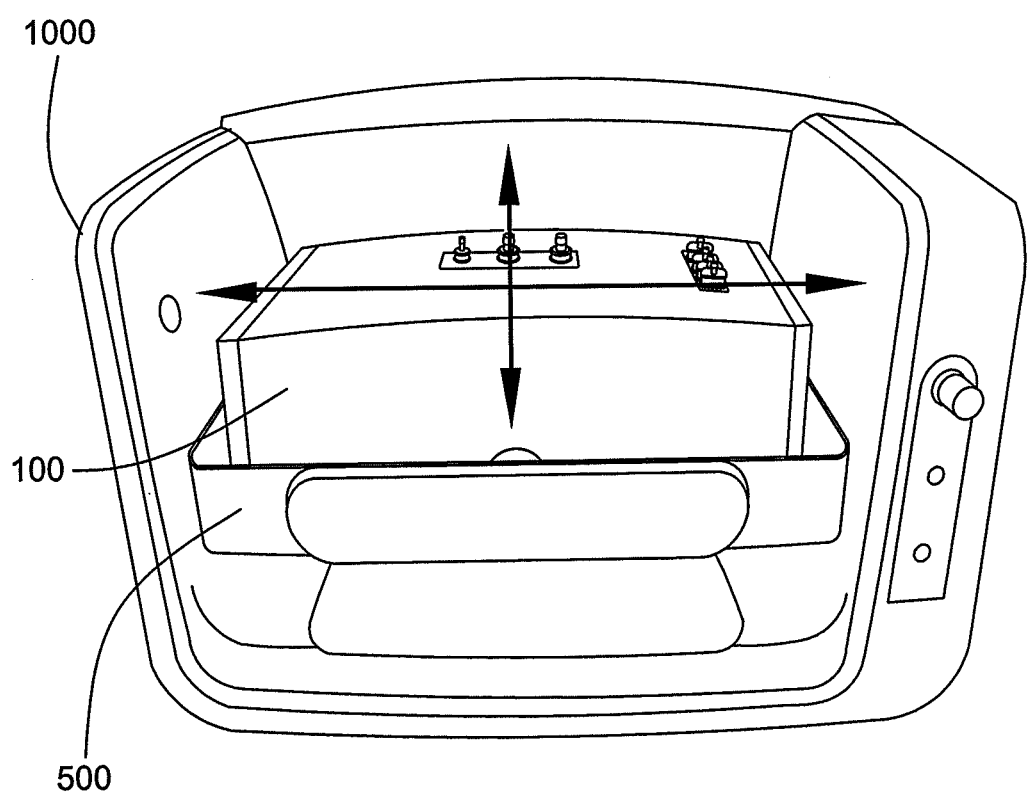
FIG. 3 shows a bioreactor on a rocking platform according to an embodiment of the present invention, also showing two rocking axes having a common center.

Subsequently, the biocontainer, containing cell culture-containing fluid (preferably, further comprising cells), is rocked, preferably, rocked along two substantially horizontal rocking axes having a common center (preferably at right angles to one another), as generally illustrated in FIG. 3.

As used herein, "releasably engaged" or "releasably engageable" means that the engagement is not permanent; rather, the bracket is engaged with the respective bracket engagement portion when desired, and the bracket is disengaged from the respective bracket engagement portion when desired. Thus, the bracket is engaged with the respective bracket engagement portion before the biocontainer is rocked, and the engagement continues while the biocontainer is rocked. However, at the desired time after rocking is completed, the bracket is disengaged from the respective bracket engagement portion, and the biocontainer is removed from the platform.

A variety of bracket and bracket engagement portion arrangements and configurations are suitable for use in the invention. While FIG. 1 shows brackets associated near the "shorter" walls of the biocontainer (side walls 16 and 18), the locations of the brackets and bracket engagement portions are not so limited. For example, embodiments of the biocontainer can include brackets near the side walls 20 and 22 (e.g., near or connected to joints or seams between side walls 20 and 22 and top and bottom walls 14 and 12, and the bracket engagement portions can be correspondingly located with respect to the rocking platform), or the brackets and/or the bracket engagement portions can be arranged vertically, e.g., as discussed below.

Figure 4:
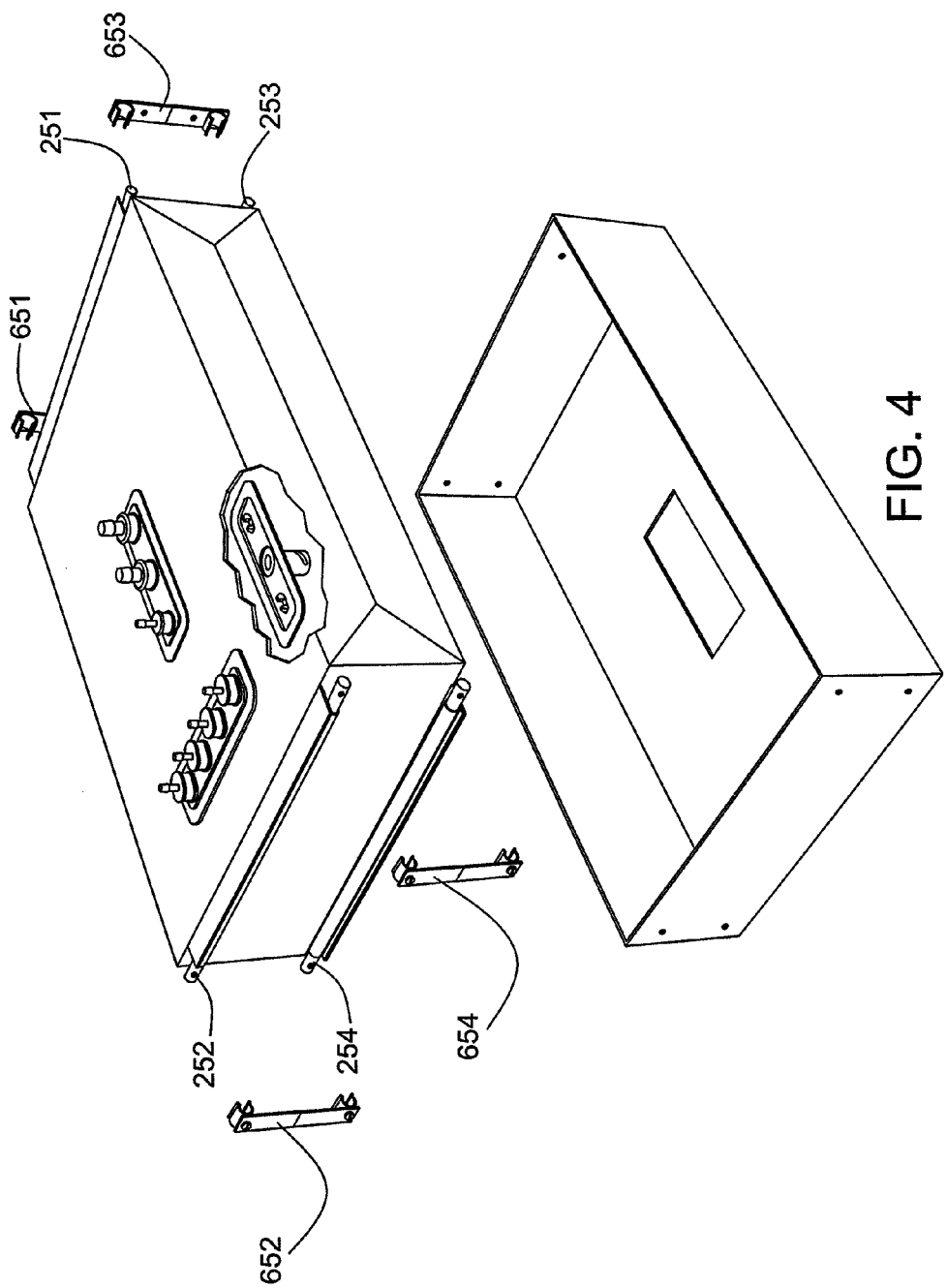
FIG. 4 shows another embodiment of a bioreactor according to the invention, comprising at least four brackets, also showing a rocking platform for receiving the bioreactors, the platform further comprising bracket engagement portions, showing a "tongue and groove" engagement.
Figure 5:
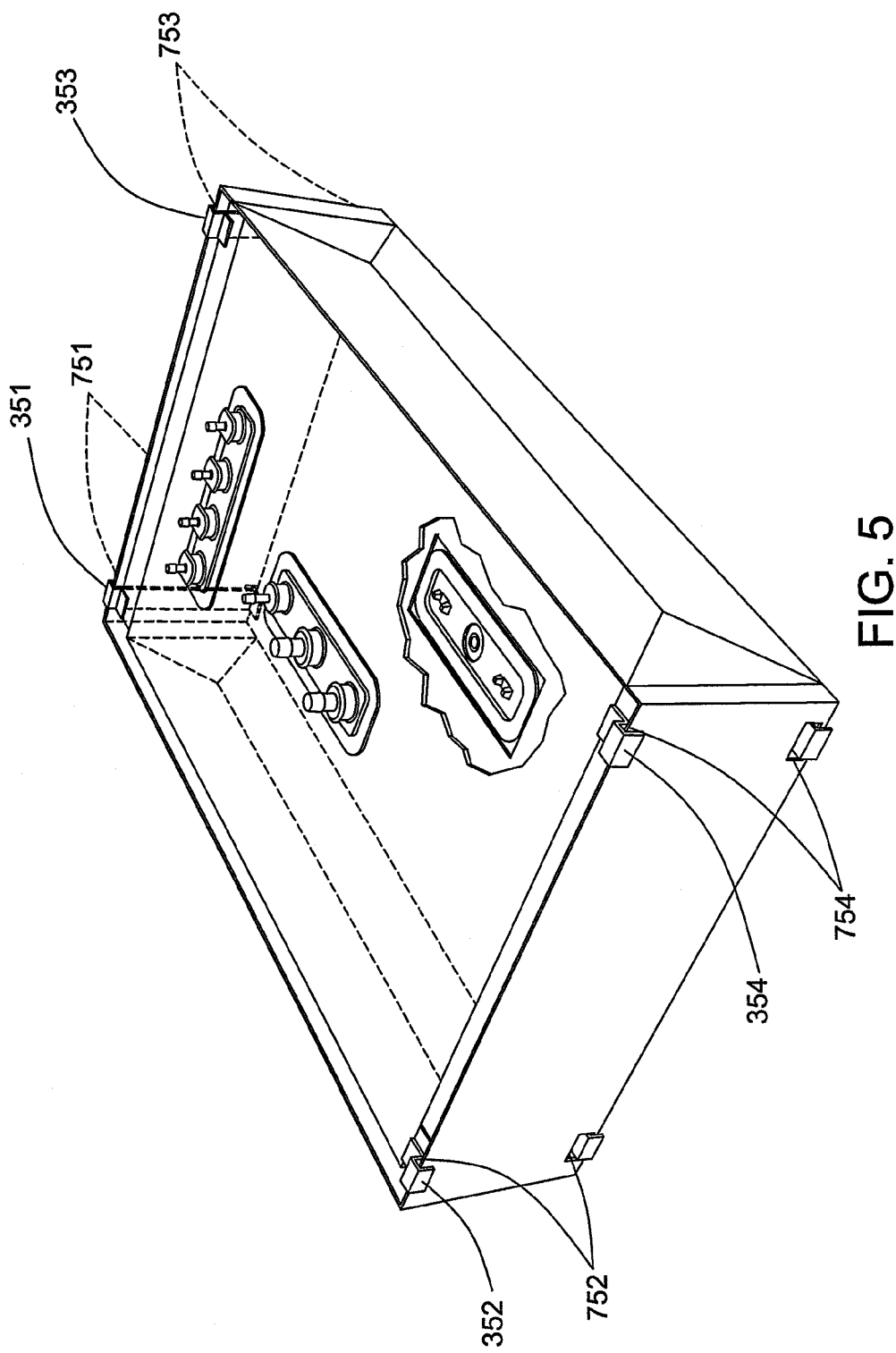
FIG. 5 shows another embodiment of a bioreactor according to the invention, comprising at least four brackets, also showing a rocking platform for receiving the bioreactors, the platform further comprising bracket engagement portions, showing brackets engaging with the platform wall edges and openings in the platform side wall.

In contrast with, for example, FIGS. 1B and 2 (and FIG. 4, discussed in more detail below), showing horizontal engageability between the brackets and bracket engagement portions, in accordance with other embodiments, e.g., as shown in FIGS. 5 and 6 (illustrating a bracket and bracket engagement portion), the engagement is vertical, and in other embodiments (not shown), at least one bracket can engage horizontally with a bracket engagement portion, and at least one other bracket can engage vertically with a bracket engagement portion.

Figure 6B:
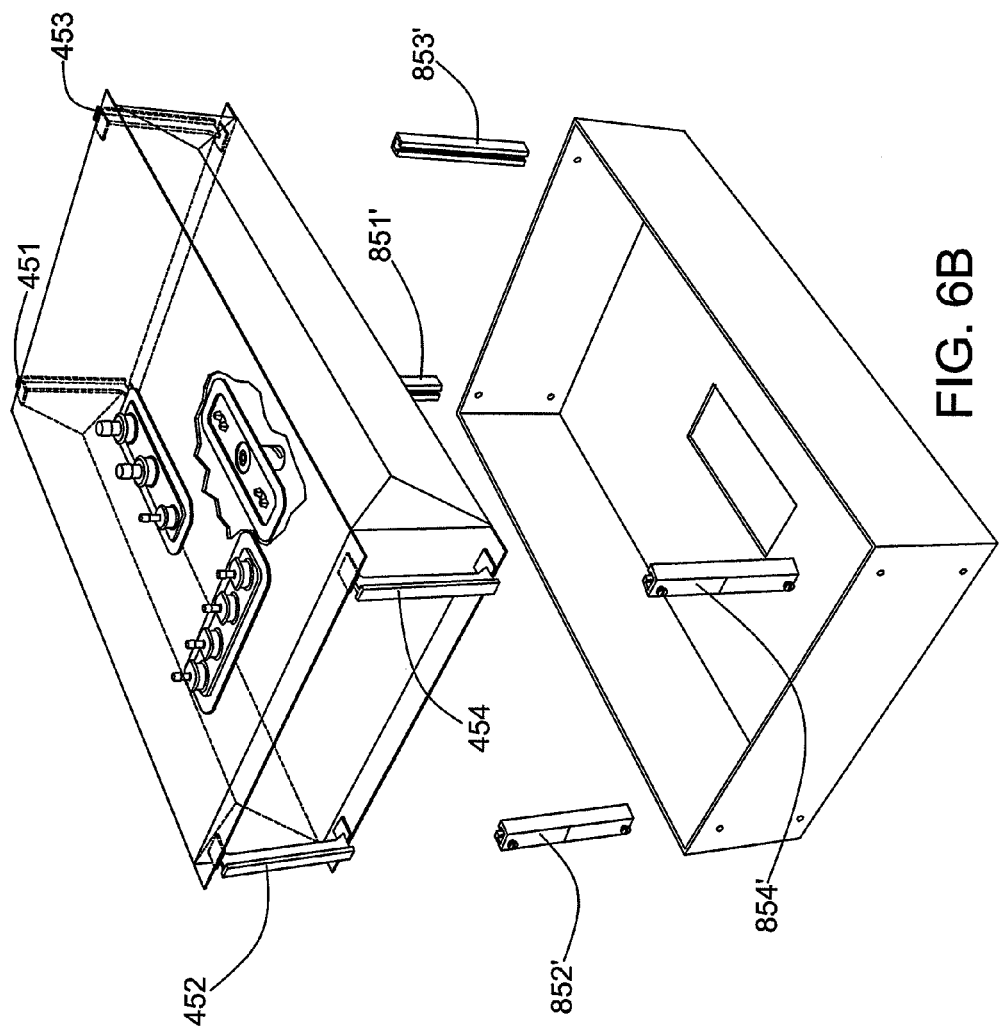
FIG. 6B shows slots mounted to the platform.

Alternatively, or additionally, in contrast with FIGS. 1B and 2, showing engageability with the platform wherein the bracket engagement portion comprises a slot closed at each end, one end including an enlarged opening, the embodiment shown in FIG. 4 shows a tongue and groove type engagement, wherein each bracket (251, 252, 253, 254) comprises a rounded tongue, and each bracket engagement portion (651, 652, 653, 654) comprises a groove (the illustrated engagement portion being shown as an element separately mountable to the platform). In accordance with the embodiment shown in FIG. 5, the brackets (351, 352, 353, 354) each comprise generally U-shaped portions at the top and bottom, releasably engageable with the platform's engagement portions (751, 752, 753, 754) each comprising platform wall edges and openings. The embodiments illustrated in FIGS. 6A and 6B show biocontainers comprising "I-" shaped brackets (451, 452, 453, 454) and platforms each comprising bracket engagement portions including slots that are open at one end (FIG. 6A shows bracket engagement portions elements (851, 852, 853, 854) integral with the platform, and FIG. 6B shows bracket engagement portions (851', 852', 853', 854') as elements separately mountable to the platform).

A bracket can comprise a sleeve and a bracket body therein, for example, in accordance with the embodiment shown in FIG. 7, each bracket (951, 952, 953, 954) comprises a bracket body (951*a*, 952*a*, 953*a*, 954*a*) including one or more lugs, wherein the bracket body is contained in a sleeve (951", 952", 953", 954"). In the embodiment shown in FIG. 7, each body comprises two projections, each projection comprising a pair of angled lugs facing in opposing directions. Thus, each bracket comprises a body, a first projection (951*b*, 952*b*, 953*b*, 954*b*) comprising a pair of first projection lugs (951*c* and 951*d*; 952*c* and 952*d*; 953*c* and 953*d*; 954*c* and 954*d*), wherein the pair of lugs face in opposing directions, and a second projection (951*b*', 952*b*', 953*b*', 954*b*') comprising a pair of second projection lugs (951*c*' and 951*d*'; 952*c*' and 952*d*'; 953*c*' and 953*d*'; 954*c*' and 954*d*'), wherein the pair of face in opposing directions, engageable with a bracket engagement slot or opening.

In accordance with yet other embodiments (not shown) the biocontainer comprises pin-shaped brackets (on side and/or bottom walls) and the platform comprises bracket engagement portions (on side and/or bottom walls) including openings without slots.

A variety of platforms are suitable for use in the invention. Preferably, the platform comprises a substantially rectangular base for supporting the bioreactor, and at least two opposing side walls, e.g., comprising bracket engagement portions and/or for attaching the bracket engagement portions. The embodiment of the platform illustrated in FIG. 2 has four side walls, wherein two of the opposing side walls comprise bracket engagement portions. Typically, the base includes at least one opening, e.g., for accommodating at least one port associated with the bottom wall of the bioreactor.

Embodiments of the bioreactor and platform can be used with any rocking apparatus. Typically, the apparatus further comprises one or more of any of the following: a motor, a pump, a drive, and a piston for rocking the platform or tray along the pivot point, e.g., along first and second substantially horizontal pivot axes that are perpendicular to one another and have a common center, for example, as generally illustrated in FIG. 3. In accordance with the invention, "perpendicular" does not require a precise 90° angle; rather, the pivot axes, having a common center, can be at angles in the range of from, for example, about 85° to about 95°. However, an angle of 90° or about 90° is preferred.

The first horizontal pivot axis has a first rocking angle and the second horizontal pivot axis has a second rocking angle. A variety of rocking angles are suitable for the first rocking angle and the second rocking angle. Typically, the rocking angles are in the range from about 1 to about 15 degrees from horizontal. The first and second rocking angles can be the same, or different.

The apparatus can also further comprise one or more of any of the following: a control unit, a speed control valve, a heater, a device (e.g., a tachometer) for monitoring and/or displaying the rocking rate(s), a sensor for monitoring and/or detecting one or more parameters (e.g., one or more of any of the following: pH, oxygen, carbon dioxide, temperature) in the biocontainer.

The rocking apparatus can be operated at any suitable frequency, for example, in the range of from about 1 to about 40 cycles per minute, or greater. Typically, the rocking apparatus is operated at a frequency of about 20 to about 30 cycles per minute.

A variety of materials are suitable for use as the sheet material forming the walls of the biocontainer. Typically, the sheet material comprises a plastic material, more typically, a multilayer plastic film. Preferably, the material used for forming the sheet material(s) of the walls of the biocontainer is compatible with the materials used for forming the ports and brackets.

A variety of materials, preferably polymeric plastic materials, are suitable for use in forming the brackets, and in some embodiments, the materials are similar to, or identical to, the materials used in forming the ports.

Preferably, the film is transparent or translucent, allowing observation of the filling and drainage of the biocontainer, e.g., so that this can be optically controlled, and allowing observation of a reaction taking place in the fluid in the biocontainer.

Polyethylene is a highly transparent polymer material easily processed to a film, and is readily available in grades containing little or no releasables or extractables. Thus, in some embodiments, at least the innermost layer of the biocontainers comprise polyethylene film layers. In one embodiment of a biocontainer according to the invention, the biocontainer includes at least two layers of polyethylene film, more preferably, wherein the innermost layer is a polyethylene film, followed by a layer of a different material, e.g., a gas barrier layer such as a barrier layer for oxygen and/or carbon dioxide, followed by another layer of polyethylene film. A gas barrier layer can be desirable for those applications wherein preventing or minimizing ingress of oxygen and/or carbon dioxide into the biocontainer.

Ethylene vinyl alcohol (EVOH) is one example of transparent or translucent material suitable for use as a bather layer.

A typical embodiment of a method for using the biocontainer is as follows. The biocontainer (in a folded state) is placed on the platform. If the biocontainer has brackets associated with the lower portion of the biocontainer, they are engaged with the corresponding bracket engagement portions of the platform.

Using the illustrative embodiment shown in FIGS. 1 and 2 for general reference, brackets 153 and 154 (FIG. 1B) are engaged with bracket engagement portions 553 and 554 (FIG. 2). Liquid cell culture media is introduced (e.g., via a pump) into the biocontainer, typically through a non-centrally arranged port arranged in the top wall (e.g., port 84), expanding the container. If the biocontainer has brackets associated with the upper portion of the biocontainer, they are engaged with the corresponding bracket engagement portions of the platform once the biocontainer is at least substantially expanded (e.g., brackets 151 and 142 (FIG. 1B) are engaged with bracket portions 551 and 552 (FIG. 2)).

Gas is introduced, e.g., through one or more gas ports arranged in the top wall (e.g., port 72), and the temperature, pH, and dissolved oxygen can be adjusted and controlled. The rocking apparatus is operated and the biocontainer is rocked along one or more axes, preferably, rocked along first and second substantially horizontal pivot axes that are perpendicular to one another. Once the desired set-points (e.g., temperature, pH, and dissolved oxygen) are reached, cells are introduced into the biocontainer (e.g., via a pump), typically through a port (e.g., port 84) arranged in the top wall.

Cell culturing and sampling can subsequently be carried out as is known in the art. For example, cell culture samples can be taken (e.g., via a liquid port arranged in the top wall, e.g., port 82) as desired, e.g., in the range of about every 12 to about every 24 hours. The sample is a suitable volume, e.g., about 10 mL.

The samples are analyzed, e.g., by determining and/or quantifying any one or more of the following: cell concentration, cell viability, pH, the desired product level (e.g., monoclonal antibody, vaccine, etc.), metabolite level (e.g., glucose level and/or lactate level).

If appropriate, the pH level is the biocontainer is adjusted/corrected by adding the appropriate reagent(s) via a port (e.g., port 81 or 83) arranged in the top wall of the container.

If appropriate, a supplement (e.g., one or more of the following: glucose, amino acid(s)) can be added to supplement certain metabolites, for example, metabolites consumed by the cells, wherein the supplement is added via a liquid port arranged in the top wall of the container (e.g., port 81 or 83). Preferably, a fed-batch process is utilized, as is known in the art, e.g., to prolong culture duration and improve product titres.

Once cell culturing has been completed, the liquid is drained from the biocontainer, typically via a port (e.g., port 64) arranged in the bottom wall of the container, and the brackets are disengaged with the bracket engagement portions. The biocontainer is removed from the platform and disposed of.

The following examples further illustrate the invention but, of course, should not be construed as in any way limiting its scope.

EXAMPLE 1

This example demonstrates that the contents of the biocontainer can be quickly and efficiently mixed with little splashing, wherein the biocontainer is rocked along two different rocking angles.

A 20 L biocontainer having four brackets is obtained as generally shown in FIG. 1, and placed on the rockable platform of the rocking apparatus as generally shown in FIGS. 2 and 3. While in the folded state (as generally shown in FIG. 1A), the brackets secured to the container near a joint between the bottom wall and the first side wall, and secured to the container near a joint between the bottom wall and the second opposing side wall, are engaged with the corresponding lower bracket engaging portions of the platform.

The biocontainer is filled with buffer solution (phosphate buffered solution (PBS)), providing an expanded biocontainer as generally shown in FIG. 1B. The brackets secured to the container near a joint between the top wall and the first side wall, and secured to the container near a joint between the top wall and the second opposing side wall, are engaged with the corresponding upper bracket engaging portions of the platform.

The biocontainer is rocked at 30 rpm, with different rocking angles along the two horizontal pivot axes having a common center. Using FIG. 3 for general reference, the long rocking angle is side to side, and the short rocking angle is front to back. The long angle is rocked at about 15° from the horizontal, and the short angle is rocked at about 5° from the horizontal.

The mixing is vigorous but with little splashing. The mixing time is 16±3 seconds.

In a comparative Example, a WAVE Cellbag™ (GE Healthcare Biosciences, Pittsburgh, Pa.) containing buffer solution is placed on a WAVE Mixer™ (GE Healthcare Biosciences, Pittsburgh, Pa.) and operated at 42 rpm, rocking the bag at a maximum of 10.4°. There is splashing of the fluid, and the mixing time is 98±9 seconds.

EXAMPLE 2

This example demonstrates that the contents of the biocontainer can be quickly and efficiently mixed with little splashing, wherein the biocontainer is rocked along two similar rocking angles along the two horizontal pivot axes having a common center.

A 20 L biocontainer having four brackets is obtained as generally shown in FIG. 1, and placed on the rockable platform of the rocking apparatus as generally shown in FIGS. 2 and 3. While in the folded state (as generally shown in FIG. 1A), the brackets secured to the container near a joint between the bottom wall and the first side wall, and secured to the container near a joint between the bottom wall and the second opposing side wall, are engaged with the corresponding lower bracket engaging portions of the platform.

The biocontainer is filled with fluid, providing an expanded biocontainer as generally shown in FIG. 1B. The brackets secured to the container near a joint between the top wall and the first side wall, and secured to the container near a joint between the top wall and the second opposing side wall, are engaged with the corresponding upper bracket engaging portions of the platform.

The biocontainer is rocked at 40 rpm, with wherein the long angle and the short angle are rocked at about 15° from the horizontal.

The mixing is vigorous but with little splashing. The $k_L a$ (1/h) (oxygen mass transfer) is 73.

In a comparative Example, a WAVE Cellbag™ containing buffer solution is placed on a WAVE Mixer™ and operated at 42 rpm, rocking the bag at a maximum of 10.4°. There is splashing of the fluid, and the $k_L a$ (1/h) is 42±1.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A biocontainer, comprising:
    a closed flexible container having a substantially rectangular cuboid form comprising a bottom wall, a top wall, first and second opposing side walls, and third and fourth opposing side walls, the side walls being joined to the top wall and the bottom wall;
    at least two ports; and
    at least first, second, third, and fourth brackets secured to the container, wherein the first bracket is secured to the container near a joint between the top wall and the first side wall, the second bracket is secured to the container near a joint between the top wall and the second opposing side wall, the third bracket secured to the container near a joint between the bottom wall and the first side wall, and the fourth bracket secured to the container near a joint between the bottom wall and the second opposing side wall, wherein each of the first, second, third, and fourth brackets comprises two projections that are spaced apart from each other, each projection comprising a pair of angled lugs facing in opposing directions away from each other, and each of the brackets is configured to reversibly engage a portion of a platform suitable for supporting the biocontainer, such that each bracket is adapted to engage the platform in at least two locations on opposing sides of the platform.

2. A method of processing a cell culture-containing fluid using the biocontainer of claim 1, the method comprising
    rocking the biocontainer on a platform along first and second substantially horizontal pivot axes that are perpendicular to one another, wherein the biocontainer contains at least a liquid culture medium and cells, and the brackets are engaged with the biocontainer during the rocking of the biocontainer.

3. The method of claim 2, further comprising removing cell-containing liquid samples from the biocontainer.

4. The method of claim 2, further comprising adjusting pH in the biocontainer.

5. The method of claim 2, wherein the first horizontal pivot axis has a first rocking angle and the second horizontal pivot axis has a second rocking angle, wherein the first rocking angle differs from the second rocking angle.

6. The method of claim 2, wherein the first horizontal pivot axis has a first rocking angle and the second horizontal pivot axis has a second rocking angle, wherein the first rocking angle is the same as the second rocking angle.

7. The method of claim 5, wherein the first rocking angle or the second rocking angle is in the range of from about 1 to about 15 degrees from horizontal.

8. The method of claim 6, wherein the first rocking angle and the second rocking angle are each in the range of from about 1 to about 15 degrees from horizontal.

9. The method of claim 2, wherein the cell culture-containing fluid comprises animal cells.

10. The method of claim 2, wherein the cell culture-containing fluid comprises microbial cells.

11. The method of claim 2, wherein the cell culture-containing fluid comprises plant cells.

12. The method of claim 2, further comprising draining at least some of the cell-culture containing fluid from the biocontainer, releasing the engagement between the brackets and the platform, and removing the biocontainer from the platform.

13. A rockable platform for rocking a biocontainer comprising:
- a rockable platform configured to receive the substantially cuboid-shaped flexible container of claim 1, wherein the rockable platform includes at least a first bracket engagement portion comprising at least two slots for receiving the two projections of the first bracket, a second bracket engagement portion comprising at least two slots for receiving the two projections of the second bracket, a third bracket engagement portion comprising at least two slots for receiving the two projections of the third bracket, and a fourth bracket engagement portion comprises at least two slots for receiving the two projections of the fourth bracket, wherein the first bracket engagement portion is arranged to engage the first bracket, the second bracket engagement portion is arranged to engage the second bracket, the third bracket engagement portion is arranged to engage the third bracket, and the fourth bracket engagement portion is arranged to engage the fourth bracket; and
- each bracket engagement portion is located on opposing sides of the rockable platform and adapted for releasable engagement with at least one of the first bracket, second bracket, third bracket, and fourth bracket in at least two locations along each bracket.

14. The rockable platform of claim 13, further comprising a heater for heating the biocontainer.

\* \* \* \* \*